US00PP08829P

United States Patent [19]

VandenBerg

[11] Patent Number: Plant 8,829

[45] Date of Patent: Jul. 12, 1994

[54] CHRYSANTHEMUM PLANT NAMED LIGHT VOLARE

[75] Inventor: Cornelis P. VandenBerg, Salinas, Calif.

[73] Assignee: Yoder Brothers, Inc., Barberton, Ohio

[21] Appl. No.: 43,489

[22] Filed: Apr. 1, 1993

[51] Int. Cl.[5] ..... A01H 5/00

[52] U.S. Cl. ..... Plt./74.1

[58] Field of Search ..... Plt. 74.1, 82.4

[56] References Cited

U.S. PATENT DOCUMENTS

| | | | |
|---|---|---|---|
| Plt. 6497 | 12/1988 | VandenBerg | Plt. 74.1 |
| Plt. 8058 | 12/1992 | VandenBerg | Plt. 74.1 |
| Plt. 8224 | 5/1993 | VandenBerg | Plt. 74.1 |
| 4,616,099 | 10/1986 | Sparkes | 47/58 |

OTHER PUBLICATIONS

Broertjes, et al., 1980, "A mutant of a mutant of a . . . Irradiation of progressive radiation-induced mutants in a mutation breeding program with *Chrysanthemum morifolium*", Euphytica, 29:526–530.

Gosling, ed., 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums The Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Light Volare particularly characterized by its flat capitulum form; daisy capitulum type; light purple ray floret color; diameter across face of capitulum of 80 to 83 mm when fully opened, when grown as a single stem spray cut mum; photoperiodic flowering response of 49 to 55 days after start of short days when grown in Salinas, Calif.; flowering response in Bogota, Colombia is 68 to 70 days; plant height is 74 to 84 cm when grown in Salinas with 3 to 11 long days prior to start of short days; height is 109 to 112 cm when grown in Bogota with 14 to 15 long days prior to start of short days; peduncle length of the first lateral at flowering after removing the apical bud and without growth regulator applications is 10 to 13 cm when grown in Salinas, and 13 to 18 cm when grown in Bogota; peduncle length of the fourth lateral at flowering is 13 to 18 cm when grown in Salinas, and 18 to 23 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Light Volare.

Light Volare, identified as 3496 (87-512A13), is a product of a mutation induction program. The new cultivar was discovered and selected by Cornelis P. VandenBerg on Nov. 28, 1990, in a controlled environment in Salinas, Calif., as one flowering plant within a flowering block established as rooted cuttings from stock plants which had been exposed as unrooted cuttings to an X-ray source of 1750 rads in Fort Myers, Fla., on Jun. 14, 1990.

The irradiated parent cultivar was the cultivar identified as Volare, disclosed in Plant Pat. No. 8,058, and described as a spray cut mum with flat capitulum form; daisy capitulum type; light purple ray floret color; diameter across face of capitulum of 80 to 83 mm when fully opened; flowering response period of 49 to 53 days after start of short days in Salinas, Calif., and 63 to 72 days in Bogota, Colombia; plant height of 74 to 99 cm when grown in Salinas with 3 to 14 long days prior to start of short days, and 99 to 114 cm when grown in Bogota with 14 to 21 long days prior to start of short days; and excellent tolerance to low night temperatures for bud initiation and flower development. The foregoing description of Volare has a somewhat wider range of measurements than the description of Volare in the noted plant patent. This is based on continued flowering trials of Volare after the patent application for Volare was prepared and filed.

The irradiation program resulting in Light Volare had as its primary objective the expansion of ray floret color ranges of the parent cultivar Volare. The irradiation program comprised irradiating cuttings of the parent cultivar at irradiation levels of 1500, 1750 and 2000 rads. A total of 1414 cuttings harvested from a total of 225 irradiated plants were planted on Sep. 24, 1990, Sep. 17, 1990 and Sep. 17, 1990, respectively. Of these, 7 initial selections were made, which selections were then revegetated and reflowered. Three consecutive flowerings resulted in discarding 4 of the original 7 selections on Aug. 9, 1991, while 3 codes were retained as PI (Possible Introduction) status. The three retained codes were further tested in Salinas, Calif., and in Bogota, Colombia, ultimately resulting in the decision to introduce two of the remaining selections as Light Volare and Blue Volare. The third remaining selection was discarded on Oct. 26, 1992. The cultivar Blue Volare is disclosed in pending application Ser. No. 08/041,495.

The first act of asexual reproduction of Light Volare was accomplished when vegetative cuttings were taken from the original selection in January 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Light Volare are firmly fixed and are retained through successive generations of asexual reproduction.

Light Volare has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and in Bogota, Colombia, under greenhouse conditions which approximate those generally used in commercial greenhouse practice. The low night temperature tolerance was determined in repeated flowerings in Bogota, Colombia, at temperatures as low as 5°-10° C.

The following traits have been repeatedly observed and are determined to be basic characteristics of Light Volare, which, in combination, distinguish this Chrysanthemum as a new and distinct cultivar:

1. Flat capitulum form.
2. Daisy capitulum type.
3. Light purple ray floret color.
4. Diameter across face of capitulum of 80 to 83 mm when fully opened, when grown as a single stem spray cut mum.
5. Photoperiodic flowering response to short days when grown in Salinas, Calif., is 49 to 55 days after start of short days. Flowering response in Bogota, Colombia is 68 to 70 days.
6. Plant height is 74 to 84 cm when grown in Salinas with 3 to 11 long days prior to start of short days; height is 109 to 112 cm when grown in Bogota with 14 to 15 long days prior to start of short days.
7. Peduncle length of the first lateral at flowering after removing the apical bud and without growth regulator applications is 10 to 13 cm when grown in Salinas, and 13 to 18 cm when grown in Bogota. Peduncle length of the fourth lateral at flowering is 13 to 18 cm when grown in Salinas, and 18 to 23 cm when grown in Bogota.
8. Excellent tolerance to low night temperatures for bud initiation and flower development.

The accompanying color photographic drawing is a front perspective view of a single stem cut spray mum of Light Volare, with the colors being as nearly true as possible with illustrations of this type.

Of the commercial cultivars known to the inventor, the most similar in comparison to Light Volare is the parent cultivar Volare. All traits of Light Volare are similar to those of Volare, except for the ray floret color and flowering response. The ray floret color of Light Volare is a significantly lighter purple than the ray floret color of Volare. In several flowering trials the flowering response of Light Volare was 1 to 2 days slower than the flowering response of Volare.

In the following description color references are made to The Royal Horticultural Society Colour Chart. The color values were determined on plant material grown as a pinched spray pot mum in Salinas, Calif. on Dec. 16, 1992.

Classification:

*Botanical.*—*Dendranthema grandiflora* cv Light Volare.

*Commercial.*—Flat daisy cut spray mum.

INFLORESCENCE

A. Capitulum:

*Form.*—Flat.

*Type.*—Daisy.

*Diameter across face.*—80 to 83 mm when fully opened.

B. Corolla of ray florets:

*Color (general tonality from a distance of three meters).*—Light purple.

*Color (upper surface).*—75C to 75D.

*Color (under surface).*—75C, overcast with 69D.

*Shape.*—Straight, slightly ribbed.

C. Corolla of disc florets:

*Color (mature).*—14B.

*Color (immature).*—144B.

D. Reproductive organs:

*Androecium.*—Present on disc florets only; moderate pollen.

*Gynoecium.*—Present on both ray and disc florets.

PLANT

A. General appearance:

*Height.*—74 to 84 cm when grown in Salinas with 3 to 11 long days prior to start of short days; height is 109 to 112 cm when grown in Bogota with 14 to 15 long days prior to start of short days.

B. Foliage:

*Color (upper surface).*—147A.

*Color (under surface).*—147B.

I claim:

1. A new and distinct Chrysanthemum plant named Light Volare, as described and illustrated.

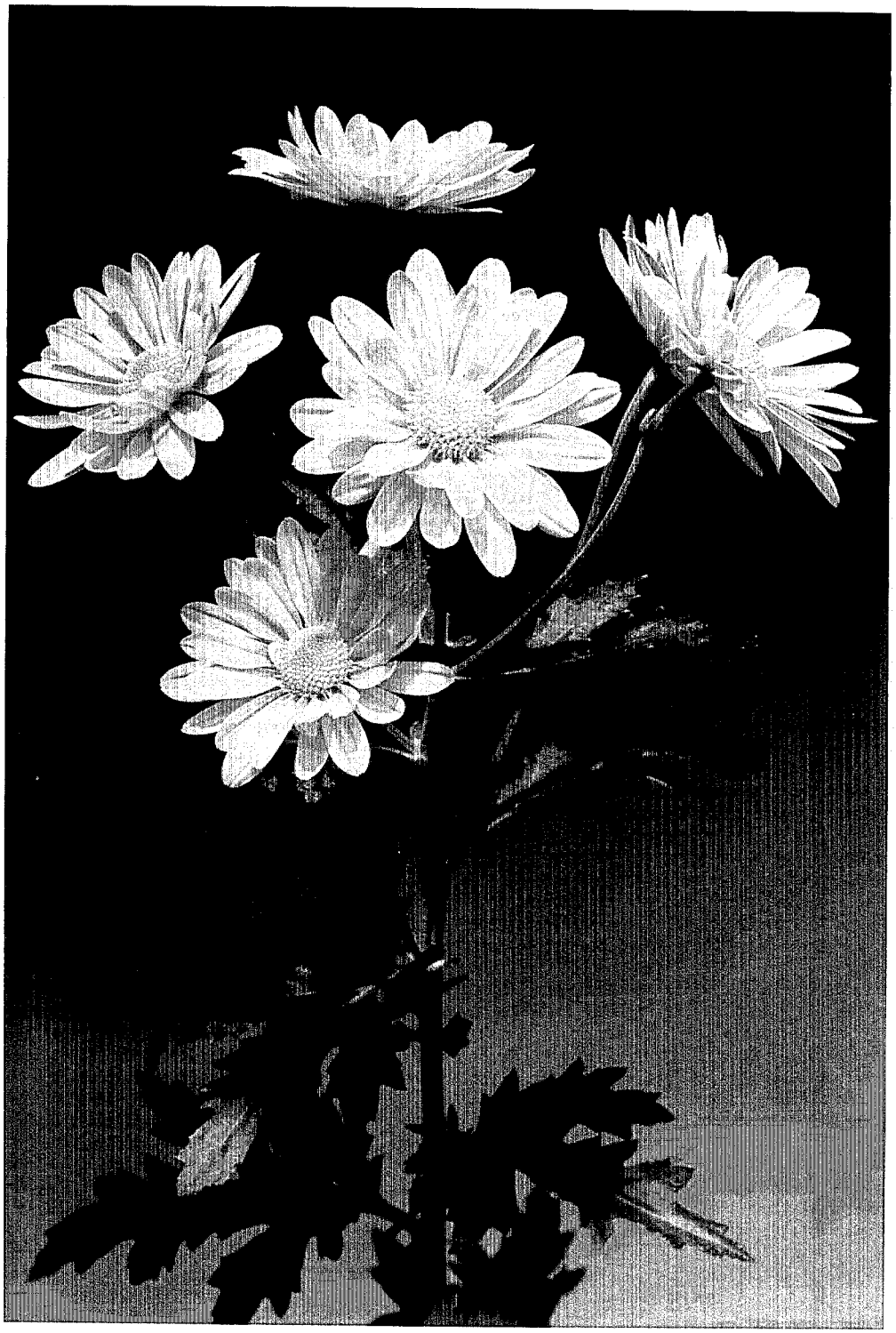

* * * * *